US009964549B2

(12) United States Patent
Katrukha et al.

(10) Patent No.: US 9,964,549 B2
(45) Date of Patent: May 8, 2018

(54) METHOD FOR DETECTION OF IGFBP-4 FRAGMENTS

(71) Applicant: HYTEST LTD., Turku (FI)

(72) Inventors: Alexey G. Katrukha, Turku (FI); Alexander B. Postnikov, Moscow (RU); Tatiana I. Solovyeva, Moscow (RU); Alexey V. Kharitonov, Moscow (RU)

(73) Assignee: HYTEST LTD., Turku (FI)

( * ) Notice: Subject to any disclaimer, the term of this patent is extended or adjusted under 35 U.S.C. 154(b) by 0 days. days.

(21) Appl. No.: 14/663,633

(22) Filed: Mar. 20, 2015

(65) Prior Publication Data

US 2015/0219671 A1  Aug. 6, 2015

Related U.S. Application Data

(62) Division of application No. 13/381,230, filed as application No. PCT/FI2010/050559 on Jun. 29, 2010, now Pat. No. 9,012,610.

(60) Provisional application No. 61/221,225, filed on Jun. 29, 2009.

(30) Foreign Application Priority Data

Jun. 29, 2009 (FI) ..................... 20095733

(51) Int. Cl.
| G01N 33/50 | (2006.01) |
| G01N 33/68 | (2006.01) |
| C07K 16/18 | (2006.01) |
| G01N 33/574 | (2006.01) |

(52) U.S. Cl.
CPC ......... G01N 33/6893 (2013.01); C07K 16/18 (2013.01); G01N 33/57407 (2013.01); G01N 33/57488 (2013.01); *C07K 2317/33* (2013.01); *G01N 2333/475* (2013.01); *G01N 2333/4745* (2013.01); *G01N 2800/32* (2013.01); *G01N 2800/324* (2013.01)

(58) Field of Classification Search
None
See application file for complete search history.

(56) References Cited

U.S. PATENT DOCUMENTS

| 5,712,103 A | 1/1998 | Leavitt et al. |
| 6,004,775 A | 12/1999 | Shimasaki et al. |

FOREIGN PATENT DOCUMENTS

| JP | 2002-511748 A | 4/2002 |
| JP | 2004-536600 A | 12/2004 |
| WO | WO 98/52597 A1 | 11/1998 |
| WO | WO 00/54806 A1 | 9/2000 |
| WO | WO 02/056015 A1 | 7/2002 |
| WO | WO 03/001881 A2 | 1/2003 |
| WO | WO 2004/045364 A2 | 6/2004 |
| WO | WO 2005/073727 A1 | 8/2005 |
| WO | WO 2009/059972 A2 | 5/2009 |

OTHER PUBLICATIONS

Chernausek et al., "Proteolytic Cleavage of Insulin-like Growth Factor Binding Protein 4 (IGFBP-4)," The Journal of Biological Chemistry (May 12, 1995), vol. 19, pp. 11377-11382.
Conover et al., "Cleavage Analysis of Insulin-like Growth Factor (IGF)-dependent IGF-binding Protein-4 Proteolysis and Expression of Protease-resistant IGF-binding Protein-4 Mutants," The Journal of Biological Chemistry (Mar. 3, 1995), vol. 270, No. 9, 4395-4400.
Fleming et al., "IGF-I differentially regulates IGF-binding protein expression in primary mammary fibroblasts and epithelial cells," Journal of Endocrinology (2005), vol. 186, pp. 165-178.
Gryup et al., "Quantification of Proteolytically Active Pregnacy-Associated Plasma Protein-A with an Assay Based on Quenched Fluorescence," Clinical Chemistry (2007), vol. 53, No. 5, pp. 947-954.
Igaku no Ayumi, "Pregnancy Associated Plasma Protein-A (PAPP-A) and Placental Growth Factor (P1GF)—Relation to the onset of acute coronary syndrome," Medical Online (2008), vol. 224, No. 5, pp. 385-388.
International Search Report dated Oct. 12, 2010, in International Application No. PCT/FI2010/050599.
Khosravi et al., "Pregnancy associated plasma protein-A: ultrasensitive immunoassay and determination in coronary heart disease,"Clinical Biochemistry 35 (2002), pp. 531-538.
Laursen et al., "Substrate specificity of the metalloproteinase pregnancy-associated plasma protein-A (PAPP-A) assessed by mutagenesis and analysis of synthetic peptides: substrate residues distant from the scissile bond are critical for proteolysis," Biochem J. (2002), vol. 367, pp. 31-40.
Monget et al., "Pregnancy-Associated Plasma Protein-A Is Involved in Insulin-Like Growth Factor Binding Protein-2 (IGFBP-2) Proteolytic Degradation in Bovine and Porcine Preovulatory Follicles . . .," Biology of Reproduction (2003), vol. 68, pp. 77-86.
Search Report dated Apr. 20, 2010, in Finnish Patent Application No. 20095733.
Ständker et al., "Partial IGF Affinity of Circulating N- and C-Terminal Fragments of Human Insulin-like Growth Factor Binding Protein-4 (IGFBP-4) and the Disulfide Bonding Pattern of the C-Terminal IGFBP-4 Domain," Biochemistry (2000), vol. 39, pp. 5082-5088.
Sun et al., "Pregnancy-Associated Plasma Protein A Proteolytic Activity Is Associated with the Human Placental Trophoblast Cell Membrane," J. Clin. Endocrinol Metab (2002), vol. 87, pp. 5235-5240.

(Continued)

*Primary Examiner* — Christine J Saoud
(74) *Attorney, Agent, or Firm* — Birch, Stewart, Kolasch & Birch, LLP

(57) ABSTRACT

Disclosed is a method for detecting IGFBP-4 (Insulin-like Growth Factor Binding Protein-4) fragments. The method uses antibodies or antigen binding fragments that specifically recognize epitopes on IGFBP-4 fragments. The IGFBP-4 fragments include the N-terminal and C-terminal fragments resulting from PAPP-A dependent cleavage of IGFBP-4. Assay and diagnostic methods using detection of IGFBP-4 fragments are also disclosed.

4 Claims, 3 Drawing Sheets

(56) References Cited

OTHER PUBLICATIONS

Zhou et al., "IGF-binding protein-4: biochemical characteristics an functional consequences," Journal of Endocinology (2003) vol. 178, pp. 177-193.

```
                          SEQUENCE LISTING

<160> NUMBER OF SEQ ID NOS: 3

<210> SEQ ID NO 1
<211> LENGTH: 16
<212> TYPE: PRT
<213> ORGANISM: Homo sapiens

<400> SEQUENCE: 1

Cys His Phe Ala Lys Ile Arg Asp Arg Ser Thr Ser Gly Gly Lys Met
1               5                   10                  15

<210> SEQ ID NO 2
<211> LENGTH: 16
<212> TYPE: PRT
<213> ORGANISM: Homo sapiens

<400> SEQUENCE: 2

Lys Val Asn Gly Ala Pro Arg Glu Asp Ala Arg Pro Val Pro Gln Cys
1               5                   10                  15

<210> SEQ ID NO 3
<211> LENGTH: 237
<212> TYPE: PRT
<213> ORGANISM: Homo sapiens
<220> FEATURE:
<221> NAME/KEY: SITE
<222> LOCATION: (135)..(136)
<223> OTHER INFORMATION: PAPP-A cleavage site

<400> SEQUENCE: 3

Asp Glu Ala Ile His Cys Pro Pro Cys Ser Glu Glu Lys Leu Ala Arg
1               5                   10                  15

Cys Arg Pro Pro Val Gly Cys Glu Glu Leu Val Arg Glu Pro Gly Cys
                20                  25                  30

Gly Cys Cys Ala Thr Cys Ala Leu Gly Leu Gly Met Pro Cys Gly Val
```

-continued

```
            35                  40                  45
Tyr Thr Pro Arg Cys Gly Ser Gly Leu Arg Cys Tyr Pro Pro Arg Gly
        50                  55                  60

Val Glu Lys Pro Leu His Thr Leu Met His Gly Gln Gly Val Cys Met
65                  70                  75                  80

Glu Leu Ala Glu Ile Glu Ala Ile Gln Glu Ser Leu Gln Pro Ser Asp
                85                  90                  95

Lys Asp Glu Gly Asp His Pro Asn Asn Ser Phe Ser Pro Cys Ser Ala
            100                 105                 110

His Asp Arg Arg Cys Leu Gln Lys His Phe Ala Lys Ile Arg Asp Arg
            115                 120                 125

Ser Thr Ser Gly Gly Lys Met Lys Val Asn Gly Ala Pro Arg Glu Asp
        130                 135                 140

Ala Arg Pro Val Pro Gln Gly Ser Cys Gln Ser Glu Leu His Arg Ala
145                 150                 155                 160

Leu Glu Arg Leu Ala Ala Ser Gln Ser Arg Thr His Glu Asp Leu Tyr
                165                 170                 175

Ile Ile Pro Ile Pro Asn Cys Asp Arg Asn Gly Asn Phe His Pro Lys
            180                 185                 190

Gln Cys His Pro Ala Leu Asp Gly Gln Arg Gly Lys Cys Trp Cys Val
        195                 200                 205

Asp Arg Lys Thr Gly Val Lys Leu Pro Gly Gly Leu Glu Pro Lys Gly
        210                 215                 220

Glu Leu Asp Cys His Gln Leu Ala Asp Ser Phe Arg Glu
225                 230                 235
```

METHOD FOR DETECTION OF IGFBP-4 FRAGMENTS

CROSS REFERENCE TO RELATED APPLICATIONS

This application is a Divisional of copending application Ser. No. 13/381,230, filed on Mar. 22, 2012, which was filed as PCT International Application No. PCT/FI2010/050559 on Jun. 29, 2010, which claims the benefit under 35 U.S.C. § 119(e) to U.S. Provisional Application No. 61/221,225, filed on Jun. 29, 2009, and under 35 U.S.C. § 119(a) to Patent Application No. 20095733, filed in Finland on Jun. 29, 2009, all of which are hereby expressly incorporated by reference into the present application.

FIELD OF THE INVENTION

The present invention describes a method for diagnosing of human diseases, including cardiovascular disease and cancer disease, which comprises detection of IGFBP-4 (insulin-like growth factor binding protein-4) fragments in patients' blood.

The present invention provides antibodies as well as epitopes for antibodies, specific to proteolytic fragments (both N- and C-terminal) of IGFBP-4 originated from IGFBP-4 molecule after its cleavage by specific protease PAPP-A. Antibodies recognizing these particular epitopes are specific to the IGFBP-4 fragments only and have no, or have low cross-reaction with the intact full-length IGFBP-4 molecule. Antibodies could be used for development of immunoassay methods for quantitative or qualitative detection of IGFBP-4 fragments in human blood.

BACKGROUND OF THE INVENTION

Insulin-like growth factor I (IGF-I) and insulin-like growth factor II (IGF-II), previously known as somatomedins, are structurally related to insulin and are the two most abundant polypeptide growth factors that circulate in human plasma (1). IGFs are multipotent growth factors responsible for normal tissue growth and regeneration. In addition, IGFs have been suggested to have beneficial effects on glucose homeostasis by its glucose lowering and insulin sensitizing actions. However, not all effects of IGFs are considered to be favorable; thus, epidemiological studies suggest that IGF-I and IGF-II are also involved in the development of common cancers, atherosclerosis and type 2 diabetes (2).

The IGFs are secreted by a number of cell types, including smooth muscle cells and macrophages. The cellular effects of the IGFs are mediated by membrane bound high affinity receptors. IGF receptors are of two distinct types and are expressed by a wide variety of cells. The IGFs are potent smooth muscle cell mitogens and it was suggested that these polypeptides contribute to the formation of the atherosclerotic lesion by paracrine, autocrine or endocrine mechanisms (3).

In plasma and other biological fluids, IGFs are complexed with proteins from the family of structurally related proteins, called IGF-binding proteins (IGFBPs). IGFBPs bind approximately 99% of the circulating IGF pool. This family of proteins includes at least six IGFBPs. IGFBPs are distinct from the IGF receptors. It is thought that IGFBPs modulate the effects of the IGFs in different tissues, including bone (4).

IGFBP-4 was initially purified from human bone cell conditioned medium as a 25 kDa protein. Later, IGFBP-4 was also purified from conditioned medium collected from a variety of cell types, and the expression of IGFBP-4 was revealed in various cell types (5, 6). The primary structure of the human IGFBP-4 protein was deduced from human placenta and osteosarcoma complementary DNA (cDNA) libraries (7, 8). The cDNA for human IGFBP-4 encodes a 258-residue protein that is processed, by removal of the signal sequence, to a mature protein of 237 residues (25.6 kDa) with a single asparagine-linked glycosylation site (7). Although various cell types when in culture secrete both glycosylated (28-29 kDa) and nonglycosylated (24-25 kDa) forms of IGFBP-4, the nonglycosylated is typically the most abundant in normal human blood (5, 6).

IGFBP-4 is unique among the six IGFBPs in having two extra cysteine residues in the variable L-domain. These unique properties of IGFBP-4 may be responsible for the distinctive biological functions of IGFBP-4 (13).

Mean level of IGFBP-4 in adult human serum is higher than those of IGFBP-1, IGFBP-2, and IGFBP-6; is similar to that of IGFBP-5; and is less than IGFBP-3 level. The trend of serum IGFBP-4 to increase with age is similar to that reported for IGFBP-1 and IGFBP-2, but is different from the declining with age levels of IGFBP-3 and IGFBP-5, suggesting that in human serum levels of the different IGFBPs are differentially regulated with advancing age (12).

Although the exact functional role for serum IGFBP-4 is not absolutely clear, in vitro studies have shown that IGFBP-4 inhibits IGF activity in bone cells and other cell types. Mohan et al. (9, 10) demonstrated that IGFBP-4 inhibited both IGF-I- and IGF-II-induced cell proliferation of embryonic chick calvaria cells and MC3T3-E1 mouse osteoblasts. IGFBP-4 inhibits IGF-I- and IGF-II stimulated the DNA synthesis in a variety of cell types (6).

IGFBP-4 synthesis may be regulated by systemic hormones and local growth factors at the transcriptional or posttranscriptional level (11). Studies in vitro revealed that parathyroid hormone, 1,25-dihydroxyvitamin D, IGF-I, IGF-II, transforming growth factor-beta, and osteogenic protein-1/bone morphogenetic protein-7 are major regulators of IGFBP-4 production in human bone cells (8,9).

Specific proteolysis is a major regulatory mechanism of IGFBP-4 functions. An IGF-dependent IGFBP-4-specific protease was first reported in the media conditioned by both human and sheep dermal fibroblasts. This protease was later identified as pregnancy-associated plasma protein-A (PAPP-A). The same proteolytic activity was also detected in the conditioned media from cultivated human osteoblasts, vascular smooth muscle cells, granulose cells, trophoblast and decidualized endometrial stromal cells, as well as in ovarian follicular fluid and human pregnancy serum (13).

PAPP-A was first isolated from human pregnancy serum in 1974 as a tetrameric complex with proform of eosinophil major basic protein (proMBP). It was revealed that PAPP-A belongs to the large metzincin family of metalloproteases. It was shown that recombinant PAPP-A is an active protease able to cleave IGFBP-4 at a single site, between M135/K136 (one letter amino acid residues code is used). IGFBP-4 cleavage by PAPP-A is possible only in case when IGFBP is complexed with IGF. PAPP-A also cleaves IGFBP-5 between S143/K144, but in this case the presence of IGF is not required.

Pregnancy associated plasma protein A was first suggested as a biological marker of atherosclerotic plaques instability after a study by Bayes-Genis et al. (16). These authors have demonstrated high levels of PAPP-A in the extracellular matrix of unstable plaques. Several studies have shown that concentration of PAPP-A in blood of patients with acute coronary syndrome (ACS) is higher than in blood of patients with stable coronary artery disease or control subjects. Thus PAPP-A was suggested as a marker of cardiovascular diseases associated with coronary artery blood clotting, such as unstable angina and myocardial infarction.

It was hypothesized that in atherosclerotic plaques PAPP-A expressed by activated smooth muscles cells could function as an active enzyme cleaving IGFBP-4 complexed with IGF, thus enhancing IGF bioavailability. The IGF system might contribute to the atherosclerotic plaque development, destabilization, and rupture leading to acute coronary events (17).

It was shown that IGFBP-4 is expressed by different cells of tumor origin, such as lung adenocarcinoma, non-small-cell lung cancer, breast cancer, colon carcinoma, follicular thyroid carcinoma, gastric cancer, glioma, hepatoma, myeloma, neuroblastoma, osteosarcoma and prostate cancer. In vitro and in vivo studies suggest that IGFBP-4 plays an important role in the growth regulation of a variety of tumors, possibly by inhibiting autocrine IGF actions. Regulation of IGF bioavailability may play crucial role in tumor growth and development (13).

Available evidences seem to suggest that plasma measurements of PAPP-A concentration could be valuable for the discrimination of patients with unstable atherosclerotic plaques as well as for identification of patients with cancer. However, it has now turned out that precise PAPP-A blood measurements are not an easy task. This is, first of all, due to the fact that there are extremely low levels of this protein in patients' plasma. It was also shown that heparin injections could also influence the PAPP-A levels in patients' plasma (18).

We have suggested that the measurements of the products of PAPP-A enzyme activity could be of higher clinical value than direct PAPP-A measurements because such products should be presented in blood in higher concentrations than PAPP-A and their concentration in blood should not be affected by heparin injections.

The present invention is devoted to the utilization of IGFBP-4 fragments as markers of increased PAPP-A activity in the body, and consequently, as markers of the different diseases associated with increased PAPP-A concentrations and activity. The immunoassay methods designed for specific measurements of proteolytic fragments of IGFBP-4 regardless of the presence of intact IGFBP-4 in patients' samples could be of practical value for the diagnosis or prediction of various pathologies including ACS and cancer.

SUMMARY OF THE INVENTION

The present invention is related to the discovery of new blood markers of human pathologies, including cardiovascular disease and cancer—proteolytic fragments of IGFBP-4.

In our studies we have shown that PAPP-A expressed in atherosclerotic plaques is an active protease. PAPP-A from atherosclerotic blood vessel was purified to homogeneity and was shown to be able effectively cleave IGFBP-4 in the presence of IGF-II. PAPP-A cleaves IGFBP-4 between amino acid residues M135 and K136, giving rise to two IGFBP-4 fragments, namely "N-terminal fragment" (comprises amino acid residues from N-terminus to M135 of intact IGFBP-4 molecule) and "C-terminal fragment" (comprises amino acid residues from K136 to C-terminus of intact IGFBP-4 molecule).

Monoclonal antibodies specific to IGFBP-4 proteolytic fragments and displaying no or low cross-reactivity with full-length molecule were obtained. These MAbs were able to recognize only novel epitopes raised by IGFBP-4 cleavage by PAPP-A between amino acid residues M135 and K136 and had no or low cross-reaction with intact (full-size) IGFBP-4 molecule. In specific, the antibodies of the invention specifically recognize novel epitopes originated by enzyme-dependent IGFBP-4 cleavage with higher affinity than they recognize full-length IGFBP-4.

Using one of these fragment-specific antibodies in pair with another antibody recognizing intact IGFBP-4, several sandwich immunoassays were designed. These assays are suitable for IGFBP-4 fragments quantification regardless to the presence of full-length IGFBP-4 in the sample (FIG. 2B).

The immunoassay methods were applied for measurement of both proteolytic fragments of IGFBP-4 in blood of ACS patients and healthy donors. It was shown that the level of IGFBP-4 proteolytic fragments was significantly higher in blood of ACS patients' than in blood of healthy donors'. Mean levels of IGFBP-4 fragments in the plasma of ACS patients were 3.2-fold higher than in plasma of healthy donors ($p<0.0005$), (FIG. 3). Basing on these observations we have suggested that both proteolytic fragments of IGFBP-4 could be used as markers of atherosclerotic plaques destabilization and rupture.

Thus in the present invention we are describing the fragments of IGFBP-4 as new marker (markers) of human pathologies, including cardiovascular disease; the method of prognosis and diagnosis of ACS using the measurements of IGFBP-4 fragments in patients' blood.

IGFBP-4 (200 ng per lane) was treated by:
Lane 1, recombinant PAPP-A;
Lane 2, atherosclerotic tissue PAPP-A;
Lane 3, without PAPP-A;
Lane 4, Molecular weight standards; shown in kDa.
Rabbit anti-IGFBP-4 polyclonal antibodies were used for immunostaining.

Figure 2A:
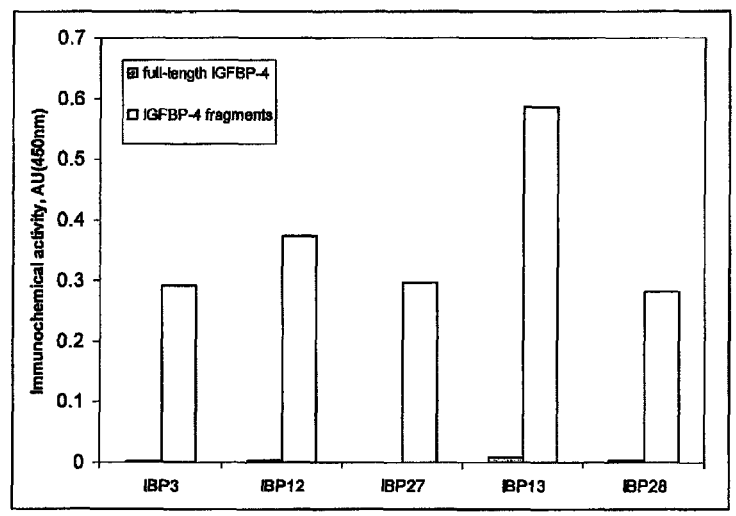

FIG. 2A. IGFBP-4 fragment-specific MAbs testing in ELISA:

10 ng of full-length recombinant IGFBP-4 or IGFBP-4 fragments produced by PAPP-A dependent cleavage were adsorbed on polystyrene plate. After washing fragment-specific MAbs IBP3, IBP12, IBP27, IBP13 and IBP28 (10 microg/ml) were incubated in wells during 30 min with shaking. Specifically bound antibodies were detected by anti-mouse IgG polyclonal antibodies, conjugate with horseradish peroxidase (substrate: TMB).

Figure 2B:
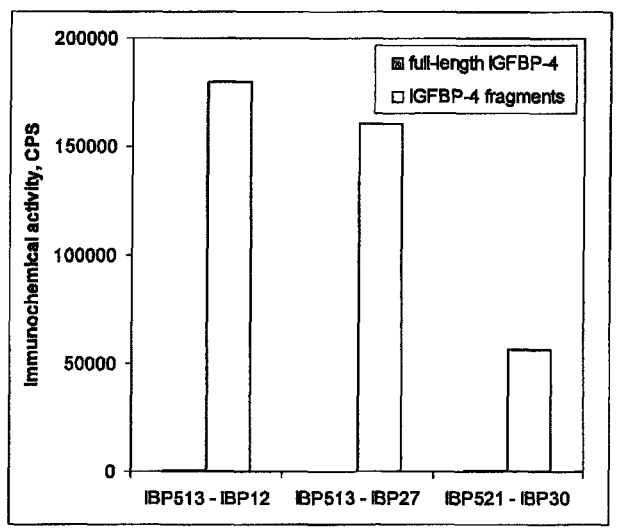

FIG. 2B. Sandwich immunoassays specific to fragments of IGFBP-4.

Immunoassays:
Capture MAbs: IBP513, IBP521 (200 ng/well).
Detection MAbs: IBP12, IBP27, and IBP30 (1 microg/ml) labeled with stable Eu3+ chelate.
Antigens: 100 ng/ml of full-length recombinant IGFBP-4 or IGFBP-4 fragments produced by PAPP-A dependent cleavage.

Incubation volume 0.1 ml.

Incubation time: 30 min at room temperature.

CPS—counts per second; AU (450 nm)—absorbance units at 450 nm.

Figure 3:
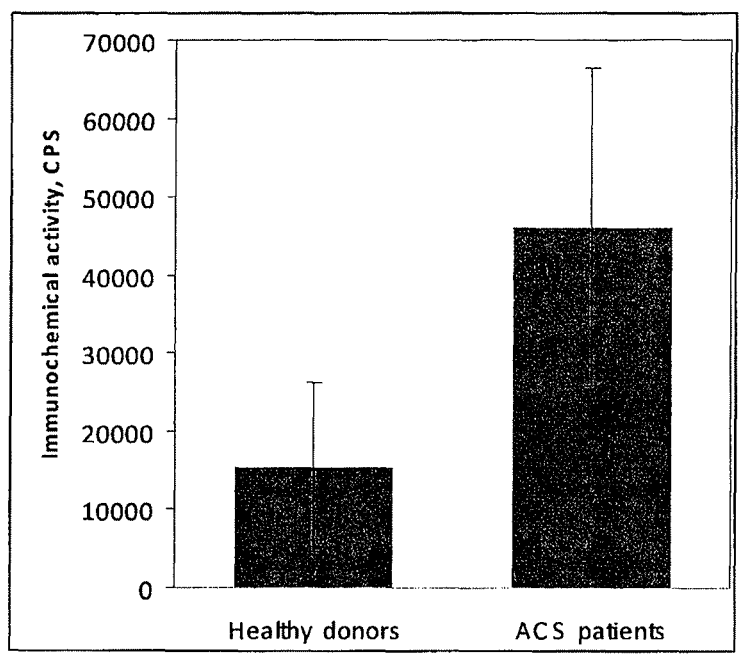

FIG. 3. IGFBP-4 fragments detection in human plasma Immunoassay:

Capture MAb: IBP521 (200 ng/well).

Detection MAb: IBP30 (1 microg/ml) labeled by stable Eu(3+) chelate.

MAB IBP521 recognizes full-size IGFBP-4 as well as its C-terminal fragment generated by PAPP-A-mediated proteolysis MAb IBP30, specifically recognizes C-terminal fragment of IGFBP-4 only and does not recognize full-size IGFBP-4.

Incubation volume 0.1 ml. Incubation time: 30 min at room temperature. CPS—counts per second.

DETAILED DESCRIPTION OF PREFERRED EMBODIMENTS

The invention describes N- and C-terminal proteolytic fragments of IGFBP-4 as the biomarkers that are presented at significantly higher levels in the plasma sample of ACS or some cancer patients in comparison with healthy donors' plasma. Immunoassays for IGFBP-4 fragments could be used for early detection of ACS or cancer, or to determine the degree of the risk of disease development.

Standard protocols were followed for the development of monoclonal antibodies specific to the IGFBP-4 peptides as well as intact IGFBP-4. Synthetic peptides used for animal immunization to obtain monoclonal antibodies, specific IGFBP-4 fragments, were corresponding to IGFBP-4 proteolytic fragments at the site of the PAPP-A-dependent cleavage. Synthetic peptides contained additional terminal cysteines (opposite to putative proteolytic site) for coupling purposes. The sequences were verified by mass spectroscopy analysis and peptides were conjugated to carrier proteins. The resulting conjugates were used as antigens for mice immunization.

Peptide-binding monoclonal antibodies are prepared according to standard technology (19-22) known to those skilled in the art. After several cycles of animal immunization mouse splenocytes are fused with cells of myeloma cell line. Such protocol includes also the stage of screening of formed hybridoma clones for desired specificity of produced antibodies. To obtain antibodies of the present invention, hybridoma clones were screened to specific binding to IGFBP-4 peptides, corresponding to IGFBP-4 proteolytic fragments, and at the same time not reacting to intact IGFBP-4. This approach enabled to find out several hybridoma clones producing monoclonal antibodies specific to novel epitopes of IGFBP-4, which were formed in the process of PAPP-A-dependent cleavage of the protein (FIG. 2A).

In the experiments made a group of monoclonal antibodies specific to proteolytic fragments of IGFBP-4, produced by PAPP-A-dependent cleavage, and having cross-reactivity to intact IGFBP-4 less than 5% was selected. However, it should be noted that the cross-reactivity percentage obtained depends on, for instance, the method used, and 5% should not be considered to be a restrictive value for low cross-reactivity.

Obtained peptide-specific antibodies were tested in sandwich immunoassay with monoclonal antibodies specific to the intact (full-size) IGFBP-4 in order to find two-site antibodies combinations, suitable for the development of sandwich immunoassays for specific determination of IGFBP-4 proteolytic fragments regardless of the presence of intact full-length IGFBP-4. Monoclonal antibodies specific to intact IGFBP-4 were used as capture antibodies, whereas monoclonal antibodies specific to proteolytic fragments of IGFBP-4 were used as detection antibodies. In some embodiments the opposite configuration of antibodies is also possible. Sandwich immunoassays described in the present invention were highly specific to proteolytic fragments of IGFBP-4 (FIG. 2B).

In the present invention the detection antibodies of developed sandwich immunoassay methods were labeled by stable Eu3+ chelate. In various other embodiments detection antibody could be labeled by different types of labels able to generate different types of signals that could be visualized or detected using a variety of standard procedures, such as detection of luminescence, chemiluminescence, fluorescence, absorbance, radioactivity, or by microscopy, imaging, etc. Immunoassays may include immunohistochemistry, enzyme-linked immunosorbent assay (ELISA), Western blotting, nephelometry, turbidimetry, immunoradiometric assay, lateral flow, immunohisto/cyto-chemistry and other methods known to those of skill in the art.

Immunoassays could be used to determine presence or absence of a biomarker in a sample as well as the amount of a biomarker in a sample. The amount of IGFBP-4 proteolytic fragments in the sample can be determined by comparison to (or as a ratio to) a reference or standard, such as an intact IGFBP-4 or different polypeptide known to be present in the sample. The amount of IGFBP-4 proteolytic fragments in the sample can also be determined by comparison to a reference or standard, such as the amount of the endogenous or recombinant or synthetic IGFBP-4 fragments in a reference or control sample. Accordingly, the amount of a biomarker in a sample need not be quantified in absolute terms, but may be measured in relative terms with respect to a reference or control.

In the present invention detection of proteolytic fragments of IGFBP-4 in the plasma samples of ACS was carried out. Significant increase of the fragments was revealed by using IBP521-IBP30 sandwich pair (FIG. 3). Various embodiments of this invention include detection of N-terminal or C-terminal, or simultaneous C-terminal and N-terminal fragments of IGFBP-4 in the patients' plasma samples for the assessment of ACS development risk.

A further embodiment of the invention is an immunoassay kit for the detection IGFBP-4 proteolytic fragments or measurement of IGFBP-4 proteolytic fragments amount in the sample. The kit may comprise (i) a monoclonal antibody specific to N-terminal or C-terminal IGFBP-4 proteolytic fragment, (ii) a second monoclonal detection antibody specific to any appropriate epitope of intact IGFBP-4, and (iii) a standard or calibrator preparation of endogenous IGFBP-4 fragments or recombinant protein corresponding at least partially to the sequence of IGFBP-4 fragment. The second monoclonal antibody may be appropriately labeled for the detection of antibody—IGFBP-4 fragments complex.

In some embodiments the kit for IGFBP-4 fragments competitive measurement may comprise (i) a monoclonal antibody specific to N-terminal or C-terminal IGFBP-4 proteolytic fragment, (ii) standard or calibrator preparation of endogenous IGFBP-4 fragments or recombinant protein corresponding at least partially to the sequence of IGFBP-4 fragment, labeled for the detection. The levels of IGFBP-4 fragments in the analyzing sample can be determined by the degree of competitive removal of the said labeled standard preparation of IGFBP-4 fragments.

EXAMPLE 1

Generation of Mouse Monoclonal Antibodies Specific to Novel Proteolysis-mediated Epitopes of IGFBP-4

Synthetic peptides obtained for mice immunization:
Peptide-1 (SEQ ID NO. 1)
Peptide-2 (SEQ ID NO. 2)

Peptide-1 and Peptide-2 were synthesized using solid-phase Fmoc chemistry (23). Peptides were prepared on p-alkoxybenzylalcohol resin. After cleavage from the resin, the crude peptide preparation was purified by reversed-phase high-pressure liquid chromatography. C18 preparative column was applied with a gradient of 0.1% trifluoroacetic acid in water and 0.1% trifluoroacetic acid in acetonitrile. The purity (>95%) was determined by analytical C18 high-pressure liquid chromatography and mass spectroscopy (matrix-assisted laser desorption/ionization mass spectrometry with accuracy±0.5 Dalton).

IGFBP-4 Peptide-1 (SEQ ID NO. 1) contained the amino acid sequence identical to IGFBP-4 fragment 121-135 of SEQ ID NO: 3, with one additional cysteine residue from the N-terminus. IGFBP-4 Peptide-2 (SEQ ID NO. 2) contained the amino acid sequence identical to IGFBP-4 fragment 136-150 of SEQ IN NO: 3 with one additional cysteine residue from the C-terminus. Sulphhydryl groups of these additional cysteine residues were used for the preparation of the peptide conjugates with carrier proteins.

Preparation of conjugates of the peptides with carrier proteins was performed by using sulfo-SMCC obtained from Pierce (Rockford, Ill.) according to manufacturer's instructions. For the conjugation 2.5 mg of carrier protein—bovine serum albumin, BSA) or ovalbumin (both obtained from Sigma Chemicals, St. Louis, Mo.) was dissolved in 10 mM $KHPO_4$, 150 mM NaCl, pH 7.4 (PBS) to the concentration 10 mg/ml. Two milligrams of sulfo-SMCC, dissolved in 0.1 ml dimethyl sulfoxide, were added to the protein solution. Reaction of carrier protein activation was carried out for 2 hours at room temperature. Excess of sulfo-SMCC was removed by gel-filtration using NAP-5 columns (obtained from GE Healthcare Life Sciences, Piscataway, N.J.). NAP-5 columns were pre-equilibrated with 10 mM $KHPO_4$, 150 mM NaCl, pH 7.2. Then 2 mg of synthetic peptide-1 or peptide-2 were added to protein solution to start the conjugation. This reaction was carried out for 2 hours on ice with constant shacking. Unreacted peptide fraction was removed from protein-peptide conjugate by using gel-filtration NAP-5 columns, pre-equilibrated with PBS. The conjugation of the peptides to appropriate carrier protein was confirmed by 3-5 kDa increase in the protein molecular weight revealed by using sodium dodecyl sulphate polyacrylamide gel electrophoresis. Conjugates were aliquoted and stored at −20° C. until use.

Immunization of Mice with of Peptide-(Carrier Protein) Conjugates

Groups of five BALB/c mice were immunized five times with peptide-protein conjugates.

Group 1: First immunization: intraperitoneally 0.2 ml of 10 microg BSA-Peptide-1 in PBS with 60% Freund's complete adjuvant; Second immunization: on day 30, intraperitoneally 0.2 ml of 5 microg BSA-Peptide-1 in PBS with 60% Freund's incomplete adjuvant; Third immunization: on day 60, intraperitoneally 0.2 ml of 2.5 microg BSA-Peptide-1 in PBS.

Group 2: First immunization: intraperitoneally 0.2 ml of 10 microg BSA-Peptide-2 in PBS with 60% Freund's complete adjuvant; Second immunization: on day 30, intraperitoneally 0.2 ml of 5 microg BSA-Peptide-2 in PBS with 60% Freund's incomplete adjuvant; Third immunization: on day 60, intraperitoneally 0.2 ml of 2.5 microg BSA-Peptide-2 in PBS.

Twenty days after third immunization mice with the highest titer of peptide-specific antibodies were selected for the last immunizations and hybridization. Mice were intravenously injected with 0.2 ml of 10 microg BSA-Peptide-1 in PBS for Group 1, and with 0.2 ml of 10 microg BSA-Peptide-2 in PBS for Group 2. Intravenous injections were repeated next day at the same protocol (fifth immunization). Then two days after the fifth immunization, spleens of immunized mice were sterilely isolated and homogenized tissue was fused with the mouse myeloma cell line sp2/0 as described previously (19-22).

Conditioned culture of growing hybridomas was screened for antibodies by enzyme linked immunosorbent assay (ELISA). Hybridomas that produced antibodies specific to Peptide-1 or Peptide-2 were selected by ELISA with ovalbumin-Peptide-1 or ovalbumin-Peptide-2, respectively, used as presorbed antigens. Human recombinant IGFBP-4 expressed in NS0 cell line (obtained form Sigma Chemicals, St. Louis, Mo.) was used as well as a presorbed antigen for the additional test. For the assay 50 ng/0.1 ml PBS per well of ovalbumin-Peptide-1, or ovalbumin-Peptide-2, or human recombinant IGFBP-4 were sorbed on the immunoassay polystyrene plates (obtained from Corning, Cambridge, Mass.). After 40 min of antigen sorption the plates were washed two times and blocked for 10 min with PBS, containing detergent Tween 20, 0.1% (PBST). Then the plates were incubated with 0.05 ml of conditioned media collected from growing hybridomas for 30 min and washed two times with PBST. Mouse antibodies bound to presorbed antigens were revealed by 30 min incubation with secondary anti-mouse IgG polyclonal antibodies, conjugated with HRP, 0.1 ml of 1:1000 dilution in PBST per well. Secondary antibodies were from Sigma Chemicals, St. Louis, Mo. After the incubation with secondary antibodies the plates were washed with PBST six times and 3,3',5,5'-tetramethyl benzidine (TMB) peroxidase substrate, containing 0.03% hydrogen peroxide, was added. The reaction was stopped after 15 minutes of incubation by adding 0.1 ml of 0.5 M phosphoric acid and absorbance in wells was measured at 450 nm. The measurement of the absorbance was performed with the Labsystems Multiscan microplate reader (Labsystems, Finland).

Hybridomas producing antibodies specific to appropriate peptide, conjugated with ovalbumin (Absorbance at described above conditions at 450 nm>0.5 over background), and at the same time not reacting with human recombinant IGFBP-4 (Absorbance at 450 nm<0.025 over background), were selected for further work. Such hybridomas were cloned by limiting dilution. Hybridoma clones secreting the monoclonal antibodies of interest were grown in Dulbecco's modified Eagle's medium (DMEM), containing 10% fetal bovine serum (HyClone Laboratories, Logan, Utah).

Affinity Purification of Antibodies

Monoclonal antibodies were raised in mouse ascitic fluid after intraperitoneal injection of selected hybridoma clones. Antibodies were purified from ascitic fluid by using Protein A affinity chromatography. The resin was from GE Healthcare Life Sciences (Piscataway, N.J.), and purification was carried out according to manufacturer's instructions. Purified monoclonal antibodies were stored as suspensions in 50% ammonium sulfate at 4° C.

Investigation of Specificity of Monoclonal Antibodies

Figure 1:
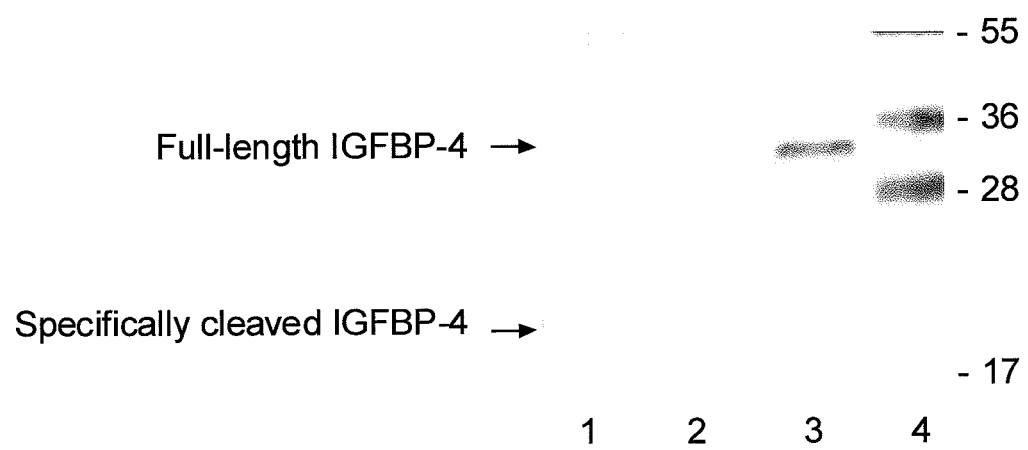
FIG. 1. Western blotting detection of proteolytic fragments of IGFBP-4 demonstrating protease activity of PAPP-A, purified from atherosclerotic tissue.

To confirm the specificity of selected monoclonal antibodies IGFBP-4 proteolytic fragments were obtained. PAPP-A-dependent proteolytic reaction was performed according to conditions described earlier (14). Two microg of human recombinant IGFBP-4 was incubated in 0.23 ml of 50 mM Tris-HCl, pH 7.5, in the presence of 2 mM $CaCl_2$, 1.8 microg IGF-II (obtained from Sigma Chemicals, St. Louis, Mo.). 40 ng of human recombinant PAPP-A (HyTest, Turku, Finland), and 2 microliters protease inhibitors cocktail (obtained from Sigma Chemicals, St. Louis, Mo.). The reaction was carried out for 15 hours at 37° C., and was stopped by freezing the sample at −20° C. The degree of PAPP-A-dependent cleavage of IGFBP-4 was determined by Western blotting by using 1 microg/ml specific rabbit polyclonal antibodies obtained from Abcam (Cambridge, Mass.) (FIG. 1).

Specificity studies of selected monoclonal antibodies to IGFBP-4 proteolytic fragments were performed in indirect ELISA using affinity-purified antibodies (FIG. 2A). Ten ng of full-length recombinant IGFBP-4 or IGFBP-4 fragments produced by PAPP-A-dependent cleavage (preparation described above) were sorbed on polystyrene plate. After 40 min of incubation the plates were washed two times and blocked for 10 min with PBS, containing detergent Tween 20, 0.1% (PBST). Then selected MAbs (10 microg/ml) were incubated for 30 min at room temperature with shaking and after that washed two times with PB ST. Specifically bound antibodies were detected by anti-mouse IgG polyclonal antibodies, conjugated with HRP, 0.1 ml of 1:1000 dilution in PBST per well. Secondary antibodies were from Sigma Chemicals, St. Louis, Mo. After incubation with secondary antibodies the plates were washed with PBST six times and 3,3',5,5'-tetramethyl benzidine (TMB)-containing peroxidase substrate, supplemented with 0.03% hydrogen peroxide, was added. The reaction was stopped after 15 minutes of incubation by adding 0.1 ml of 0.5 M phosphoric acid and absorbance was measured at 450 nm. The group of monoclonal antibodies specific to proteolytic fragments of IGFBP-4, produced by PAPP-A-dependent cleavage, and having cross-reactivity to intact IGFBP-4 less than 5% was finally selected: IBP28, IBP27, IBP12, IBP3, IBP4, IBP7, IBP13, IBP18, IBP19, IBP20, IBP30, IBP167, IBP166, IBP168, IBP174, IBP160, IBP161, IBP164, IBP171. All monoclonal antibodies were of IgG isotype, except that IBP30 was of IgM isotype.

Design of Sandwich Immunoassays for Quantification of IGFBP-4 Fragments

Specificity of affinity-purified monoclonal antibodies was also checked in sandwich immunoassays (FIG. 2B). Several sandwich assays utilizing one monoclonal antibody specific to proteolytic fragment of IGFBP-4 (N- or C-terminal; cross-reaction with full-length molecule less than 5% in indirect ELISA) and another MAb, recognizing any epitope of intact IGFBP-4, were developed. Generation of mouse monoclonal antibodies specific to intact IGFBP-4 is described in Example 2.

To perform sandwich fluorescent immunoassays, we used detection MAbs labeled with stable Eu3+ chelate as described by Hyytiä et al. (24). Capture antibodies in this assay were specific to intact IGFBP-4, whereas detection antibodies were specific to proteolytic neo-epitopes of IGFBP-4. Capture antibodies (IBP513, IBP521), 2 µg per well in 100 µL of phosphate buffer saline, were incubated in 96-well immunoassay plates for 30 min at room temperature upon constant shaking. The plates were washed with 10 mM Tris-HCl (pH 7.8) buffer, supplemented by 0.15 M NaCl, 0.025% Tween 20 and 0.5 g/l $NaN_3$ (buffer A). After washing 0.1 ml of assay buffer (50 mM Tris-HCl buffer, pH 7.7, 9 g/l NaCl, 0.01% Tween 40, 0.5% BSA and 0.5 g/l $NaN_3$), containing 100 ng/ml of full-length human recombinant IGFBP-4 or IGFBP-4 fragments produced by PAPP-A-dependent cleavage were added to the plates. The plates were incubated for 30 min at room temperature with constant shaking. After washing with buffer A 0.1 ml of the solution (1 mg/l) of detection antibodies (IBP12, IBP27 and IBP30) in the Assay buffer were added. The plates were incubated for 30 min at room temperature with constant shaking. After washing with buffer A, 0.2 ml of Enhancement solution (1.75 M NaSCN, 1 M NaCl, 5% glycerol, 20% 1-propanol, 5 mM $Na_2CO_3$, 50 mM glycine-NaOH, pH 10.0) per well ware added and incubated for 3 min at room temperature with gentle shaking. Fluorescence of Eu3+ was measured on a Victor 1420 multilabel counter (Wallac-Perkin Elmer). The fluorescence was expressed in counts per second (CPS).

Developed sandwich immunoassays were able to detect only IGFBP-4 fragments produced by PAPP-A-dependent cleavage and had no crossreaction (or very low—less than 1%) with full-length IGFBP-4.

EXAMPLE 2

Generation of Mouse Monoclonal Antibodies Specific to Intact IGFBP-4

Immunization of Mice

Five BALB/c mice were immunized five times with human recombinant IGFBP-4 expressed in mammalian NS0 cell line. The protein was obtained from Sigma Chemicals, St. Louis, Mo. First immunization: intraperitoneally 0.2 ml of 5 microg IGFBP-4 in PBS with 60% Freund's complete adjuvant. Second immunization: on day 30, intraperitoneally 0.2 ml of 2 microg IGFBP-4 in PBS with 60% Freund's incomplete adjuvant. Third immunization: on day 60, intraperitoneally 0.2 ml of 2 microg IGFBP-4 in PBS.

Twenty days after third immunization mice with the highest titer of protein-specific antibodies were selected for the following immunizations and hybridization. Mice were intravenously injected for a fourth time with 0.2 ml of 2 microg IGFBP-4 in PBS. The last intravenous injection was performed on the next day according to the same protocol (fifth immunization). Two days later, spleen of immunized mice was sterilely isolated and homogenized tissue was fused with the mouse myeloma cell line sp2/0 as described previously (19-22).

Conditioned media of growing hybridomas was screened for IGFBP-4-specific antibodies using ELISA method. Hybridomas producing antibodies specific to intact IGFBP-4 were selected by means of indirect ELISA. For the assay 50 ng/0.1 ml PBS per well of full-length human recombinant IGFBP-4 were sorbed on the immunoassay polystyrene plates. After 40 min of incubation the plates were washed two times and blocked for 10 min with PBS, containing detergent Tween 20, 0.1% (PBST). Then the plates were incubated for 30 min with 0.05 ml of conditioned media collected from wells containing growing hybridomas. After incubation the plates were washed two times with PBST. After washing the plates were incubated with 0.1 ml of per well of secondary anti-mouse IgG polyclonal antibodies, conjugated with HRP (1:1000 dilution in PBST) for 30 min. After incubation with secondary antibodies the plates were washed with PBST six times and peroxidase substrate, containing TMB and 0.03% hydrogen peroxide, was added. The reaction was stopped after 15 minutes of incubation by adding 0.1 ml of 0.5 M phosphoric acid and the absorbance in wells was measured at 450 nm.

Hybridomas producing antibodies specific to full-length IGFBP-4 (absorbance at described above conditions at 450 nm>0.5 over background) were cloned by limiting dilution method. Hybridoma clones secreting the monoclonal antibodies of interest were cultivated in DMEM, containing 10% fetal bovine serum.

Affinity Purification of Antibodies

Monoclonal antibodies specific to full-length IGFBP-4 were raised in mouse ascitic fluid after intraperitoneal injection of selected hybridoma clones. Antibodies were purified from ascitic fluid by using Protein A affinity chromatography. The resin was from GE Healthcare Life Sciences (Piscataway, N.J.), and purification was carried out according to manufacturer's instructions. Purified monoclonal antibodies were stored as suspensions in 50% ammonium sulfate at 4° C.

EXAMPLE 3

Proteolytic Activity of Atherosclerotic PAPP-A

Samples of human atherosclerotic coronary vessels were stored at −70° C. until used. PAPP-A was extracted from atherosclerotic coronary arteries after tissue homogenization in 50 mM Tris-HCl (pH 7.8) buffer, containing 0.15 M NaCl, 0.5% Triton X100, and protease inhibitors cocktail. Extracted PAPP-A was purified by means of affinity chromatography. Affinity matrix used for PAPP-A purification was prepared utilizing PAPP-A-specific monoclonal antibody 4G11 (obtained from HyTest, Turku, Finland). To confirm identity of purified protein to PAPP-A, Western blotting analysis with several PAPP-A-specific monoclonal antibodies and liquid chromatography/tandem mass spectrometry analysis were used.

For proteolytic activity analysis of atherosclerotic PAPP-A 2 microg of human recombinant IGFBP-4 was incubated in 0.23 ml of 50 mM Tris-HCl, pH 7.5, in the presence of 2 mM $CaCl_2$, 1.8 microg IGF-II (obtained from Sigma Chemicals, St. Louis, Mo.), 40 ng of atherosclerotic PAPP-A, and 2 microliters protease inhibitors cocktail (obtained from Sigma Chemicals, St. Louis, Mo.). The reaction was carried out for 15 hours at 37° C., and was stopped by freezing of the sample at −20° C. The degree of PAPP-A-dependent cleavage of IGFBP-4 was determined by Western blotting using IGFBP-4-specific rabbit polyclonal antibodies (obtained from Abcam, Cambridge, Mass.) (FIG. 1). Atherosclerotic PAPP-A was shown to cleave IGFBP-4 with the same efficiency as recombinant PAPP-A. Thus, for the first time it was shown that endogenous PAPP-A expressed in human plaques is an active protease that is able to cleave IGFBP-4 in the presence of IGF-II.

EXAMPLE 4

Measurement of IGFBP-4 Fragments in ACS Patients' Plasma Samples

Blood of 43 patients with ACS (with ST-segment elevation) as well as plasma samples from 34 healthy donors were tested by fragment-specific sandwich immunoassays. All plasma samples were collected from the patients in the presence of EDTA and were stored at −70° C. before measurements.

For the sandwich immunoassay measurements capture antibody IBP521, 2 microg per well in 0.1 ml of phosphate buffer saline, was incubated in 96-well immunoassay plates for 30 min at room temperature upon constant shaking. After washing with buffer A, 0.1 ml of patients' plasma samples diluted 1:1 with the Assay buffer were added to the plates. Plates were incubated for 30 min at room temperature with constant shaking. After washing with buffer A 0.1 ml detection antibody IBP30 (1 mg/l) in the Assay buffer was added. The plates were incubated for 30 min at room temperature with constant shaking. After washing with buffer A, 0.2 ml of Enhancement solution per well was added and incubated for 3 min at room temperature with gentle shaking. Fluorescence of Eu3+ was measured using a Victor 1420 multilabel counter (Wallac-Perkin Elmer). The level of IGFBP-4 fragments in the plasma of ACS patients was 3.2-fold higher (p<0.0005) than in plasma of healthy donors (FIG. 3). Mean values±Standard Deviation are shown at the figure. The fluorescence was expressed in counts per second (CPS).

REFERENCES

1. Spencer E M. Modern concepts of insulin-like growth factors. New York: Elsevier, 1991.
2. Frystyk J., Free insulin-like growth factors—measurements and relationships to growth hormone secretion and glucose homeostasis. Growth Horm IGF Res. 2004; 14(5):337-75.
3. Ferns G A et al. The insulin-like growth factors: their putative role in atherogenesis. Artery 1991; 18(4):197-225.
4. Rosenfeld R G, Lamson G, Pham H, Oh Y, Conover C, De Leon D D, Donovan S M, Ocrant I, Giudice L. Insulin-like growth factor-binding proteins. Recent Prog Horm Res. 1990; 46:99-159.
5. Baxter R C, Martin J L. Binding proteins for the insulin-like growth factors: structure, regulation and function. Prog in Growth Factor Res. 1989; 1:49-68.
6. Rechler M M., Insulin-like growth factor binding proteins. Vitam Horm. 1993; pp. 471-114.
7. La Tour D, Mohan S, Linkhart T A, Baylink D J, Strong D D. Inhibitory insulin-like growth factor binding protein: cloning, complete sequence, and physiologic regulation. Mol Endocrinol. 1990; 4:1806-1814.
8. Shimasaki S, Uchiyama F, Shimonaka M, Ling N., Molecular cloning of the cDNAs encoding a novel insulin-like growth factor binding protein from rat and human. Mol Endocrinol. 1990, 4:1451-1458.
9. Mohan S, Bautista C, Wergedal J, Baylink D J. Isolation of an inhibitory insulin-like growth factor (IGF) binding protein from bone cell conditioned medium: a potential local regulator of IGF action. Proc Nat Acad Sci USA. 1989; 86:8338-8342.
10. Mohan S, Nakao Y, Honda Y, et al., Studies on the molecular mechanisms by which insulin-like growth factor (IGF) binding protein-4 (IGFBP-4) and IGFBP-5 modulate IGF actions in bone cells. J Biol Chem. 1995; 270:20424-20431.
11. Mohan S, Strong D D, Linkhart T A, Baylink D J. Regulation and actions of insulin-like growth factor binding protein (IGFBP-4 and IGFBP-5 in bone: physiological and clinical implications. In: Baxter R C, Gluckman P D, Rosenfeld R G, eds. The insulin-like growth factors and their regulatory proteins. Excerpta Medica; 1994; 205-215.
12. Honda Y, Landale E C, Strong D D, Baylink D J., Recombinant Synthesis of Insulin-Like Growth Factor-Binding Protein-4 (IGFBP-4): Development, Validation, and Application of a Radioimmunoassay for IGFBP-4 in Human Serum and Other Biological Fluids. Journal of Clinical Endocrinology and Metabolism 1996; 81(4): 1389-1396.
13. Zhou R, Diehl D, Hoeflich A, Lahm H, Wolf E., IGF-binding protein-4: biochemical characteristics and functional consequences. Journal of Endocrinology 2003; 178: 177-193.
14. Overgaard M T, Haaning J, Boldt H B, Olsen I M, Laursen L S, Christiansen M, Gleich G J, Sottrup-Jensen L, Conover C A, Oxvig C Expression of recombinant human pregnancyassociated plasma protein-A and identification of the proform of eosinophil major basic protein as its physiological inhibitor. Journal of Biological Chemistry, 2000; 275: 31128-31133.
15. Bayes-Genis A, Conover C A, Schwartz R S. The insulin-like growth factor axis: A review of atherosclerosis and restenosis. Circ Res. 2000; 86:125-30.
16. Bayes-Genis A, Conover C A, Overgaard M T, Bailey K R, Christiansen M, Holmes D R Jr, et al. Pregnancy-associated plasma protein A as a marker of acute coronary syndromes. N Engl J Med. 2001; 345:1022-9.
17. Libby P, What happens inside an atherosclerotic plaque? International Congress Series, 2004; 1262 253-256
18. Wittfooth S, Qin Q, Pettersson K., Perfomance of immunofluorometric point-of-care assays for free pregnancy-associated plasma protein A detection in whole blood samples. Clin Chem Lab Med; 2008; 46 (1)18-20
19. Köhler G, Milstein C., Continuous cultures of fused cells secreting antibody of predefined specificity. Nature. 1975; 256(5517):495-7.
20. Köhler G, Milstein C., Derivation of specific antibody-producing tissue culture and tumor lines by cell fusion. Eur J Immunol. 1976; 6(7):511-9.
21. Köhler G, Howe S C, Milstein C., Fusion between immunoglobulin-secreting and nonsecreting myeloma cell lines. Eur J Immunol. 1976; 6(4):292-5.
22. Hammerling, G. J., Hammerling, U., and Kearney, J. F. eds., Monoclonal Antibodies and T-Cell Hybridomas, published by Elsevier, North-Holland, New York, 1981; pp. 563-587.
23. Fields C G, Fields G B, Noble R L, Cross T A., Solid phase peptide synthesis of 15N-gramicidins A, B, and C and high performance liquid chromatographic purification. Int J Pept Protein Res. 1989; 33(4):298-303.
24. Hyytiä H, Ristiniemi N, Airas L, Pettersson K, Hellman J, Development of an immunoassay for the detection of cystatin C dimers. J Immunol Methods 2010; 355(1-2): 14-20.

The invention claimed is:

1. A method for detecting IGFBP-4 fragments in a sample, said method comprising the steps of:
    contacting an isolated antibody or an antigen-binding fragment thereof with at least one IGFBP-4 fragment, wherein the isolated antibody or an antigen-binding fragment thereof binds an epitope located within an IGFBP-4 protein fragment consisting of amino acid residues 121-135 of SEQ ID NO: 3 or an epitope located within an IGFBP-4 protein fragment consisting of amino acid residues 136-150 of SEQ ID NO: 3 wherein the antibody or antigen binding fragment has a cross-reactivity to intact IGFBP-4 of less than 5%; and
    performing an immunoassay.

2. The method according to claim 1, wherein the antibody is a monoclonal antibody or a recombinant antibody.

3. The method according to claim 1, further comprising the steps of:
    a) providing a sample containing the IGFBP-4 fragment as a sample IGFBP-4 fragment;
    b) preparing a calibration curve using a standard IGFBP-4 fragment; and
    c) comparing the sample IGFBP-4 fragment detected by the isolated antibody or antigen-binding fragment to the calibration curve to determine the quantity of the sample IGFBP-4 fragment in the sample.

4. The method of claim 1, wherein the immunoassay is one or more selected from the group consisting of sandwich immunoassay, immunohistochemistry, enzyme-linked immunosorbent assay (ELISA), Western blotting, nephelometry, turbidimetry, immunoradiometric assay, lateral flow, and immunohisto/cyto-chemistry.

* * * * *